United States Patent [19]
Bertocchio et al.

[11] Patent Number: 6,039,845
[45] Date of Patent: *Mar. 21, 2000

[54] PROCESS FOR THE PURIFICATION OF PENTAFLUOROETHANE BY EXTRACTIVE DISTILLATION

[75] Inventors: Rene Bertocchio; Eric Lacroix; Sylvain Perdrieux, all of Puteaux, France

[73] Assignee: Elf Atochem S.A., France

[*] Notice: This patent is subject to a terminal disclaimer.

[21] Appl. No.: 09/002,344

[22] Filed: Jan. 2, 1998

[30] Foreign Application Priority Data

Jan. 6, 1997 [FR] France ................................ 97 00053

[51] Int. Cl.⁷ .......................................................... B01D 3/34
[52] U.S. Cl. ............................... 203/57; 203/67; 203/100; 570/178
[58] Field of Search .............................. 203/57, 67, 100; 570/178, 177

[56] References Cited

U.S. PATENT DOCUMENTS

| | | |
|---|---|---|
| 5,087,329 | 2/1992 | Felix . |
| 5,200,431 | 4/1993 | Dattani et al. . |
| 5,346,595 | 9/1994 | Clemmer et al. . |

FOREIGN PATENT DOCUMENTS

| | | |
|---|---|---|
| 0 508 631 A1 | 10/1992 | European Pat. Off. . |
| 0 626 362 A1 | 11/1994 | European Pat. Off. . |
| 2 716 449 | 8/1995 | France . |
| 2001414 | 1/1990 | Japan . |
| 9220640 | 11/1992 | WIPO . |
| WO 95/21147 | 8/1995 | WIPO . |
| WO 95/21148 | 8/1995 | WIPO . |
| WO 96/06063 | 2/1996 | WIPO . |
| WO 96/07627 | 3/1996 | WIPO . |

OTHER PUBLICATIONS

Chang–Ming Hu and Ming–Hu Tu, Journal of Fluorine Chemistry, vol. 55, pp. 105–107 (1991).

French Search Report dated Sep. 10, 1997.

*Primary Examiner*—Virginia Manoharan

[57] ABSTRACT

A process for the purification of pentafluoroethane (F125) containing chloropentafluoroethane (F115). The F125–F115 mixture to be purified is subjected to an extractive distillation, the extractant being a $C_5$–$C_8$ perfluoroalkyl halide.

3 Claims, No Drawings

6,039,845

PROCESS FOR THE PURIFICATION OF PENTAFLUOROETHANE BY EXTRACTIVE DISTILLATION

FIELD OF THE INVENTION

The invention relates to the purification of pentafluoroethane (F125) containing chloropentafluoroethane (F115), and its subject-matter is more particularly a purification process in which the F115 is removed by extractive distillation and easily recovered with a view to being subsequently converted into products which are harmless to the earth's atmosphere.

BACKGROUND OF THE INVENTION

Pentafluoroethane is one of the possible replacements for chlorofluorocarbons (CFCs) to which the Montreal Protocol applies and which are characterized by an exceptionally long lifetime, enabling them to reach the high layers of the atmosphere and thus to contribute, under the influence of the UV radiation, to the destruction of the ozone layer. It is therefore obvious that their replacements must contain only traces of these CFCs, depending on the various processes for obtaining them.

The replacements are generally obtained either by appropriate fluorination methods, which are not highly selective and can give rise to perhalogenated compounds of the CFC type by disproportionation, or from CFCs themselves by reduction methods, in practice by hydrogenolysis reactions. Pentafluoroethane (F125) can thus be prepared by fluorination of perchloroethylene or of its intermediate fluorination products such as dichlorotrifluoroethane (F123) and chlorotetrafluoroethane (F124) or by hydrogenolysis of chloropentafluoroethane (F115). In both cases the F125 produced contains significant quantities of F115 which must be removed as completely as possible, since F115 is a CFC.

However, the existence of an F115/F125 azeotrope containing 21 % by weight of F115 (see U.S. Pat. No. 3,505,233) with a boiling point (−48.5° C. at 1.013 bar) very close to that of F125 (−48.1° C.) makes complete separation of F115 and of F125 by distillation practically impossible unless technically complex procedures are employed, such as azeotropic distillation at various pressures, as described in U.S. Pat. No. 5,346,595. The removal of F115 from F125 can therefore be done only by a chemical route or by physical methods involving a third substance.

In patent application EP 508 631, which describes the production of hydrofluorocarbons (HFCs) by liquid-phase chemical reduction of chlorine, bromine or iodine compounds with a metal hydride or a complex of such a hydride, it is indicated that this process can be advantageous for purifying some HFCs like F125. For the same purpose, Japanese patent application (Kokai) published under No. 2001414/90 employs metal redox couples in a solvent medium. Other techniques, like that described in Journal of Fluorine Chemistry, 1991 vol. 55, p. 105–107, employ organic reducing agents such as ammonium formate in DMF medium and in the presence of ammonium persulphate.

These processes, which make use of reactants that are difficult to handle (metal hydrides) or are liable to present effluent problems, are not very compatible with industrial production of F125 in large tonnages.

For industrial manufacture of F125 the extractive distillation technique appears to be the ideal process for removing the residual F115.

In an extractive distillation process the separation of the constituents of a binary mixture is done with the aid of a so-called extraction column comprising successively, from the boiler to the top, three sections, one for exhaustion, the second for absorption and the third for recovery.

The binary mixture to be fractionated is injected at the top of the exhaustion section while the third substance acting as a selective solvent is introduced at the top of the absorption section so as to travel in the liquid state from its point of introduction to the boiler.

The third, so-called recovery section is used to separate by distillation the least absorbed constituent, from the traces of solvent which are entrained under the effect of its vapour pressure, which is not zero.

The application of this technique to the purification of 1,1,1,2-tetrafluoroethane (F134a) has formed the subject-matter of U.S. Pat. No. 5,200,431; the extractant employed is a chlorinated solvent or an aliphatic hydrocarbon.

The application of extractive distillation to the purification of F125 is already described in a number of documents including U.S. Pat. No. 5,087,329, which employs as extractant a $C_1$–$C_4$ fluorohydrocarbon optionally containing hydrogen and/or chlorine atoms and which has a boiling point of between −39 and +50° C. According to the data in this patent, dichlorotetrafluoroethanes (F114 and F114a) are at least three times more efficient than the other compounds cited. Furthermore, 5 of the 8 solvents cited are CFCs to which the Montreal Protocol applies and whose commercial availability should cease in the near future.

Industrial use of the process according to the patent can therefore be envisaged economically only when the extractant used forms part of the chain of inter-mediates leading to F125, that is to say actually in the processes for the preparation of F125 by hydrogenolysis.

In the case of manufacture of F125 by fluorination of perchloroethylene or of its partial fluorination products (F122, F123, F124), U.S. Pat. No. 5,087,329 leaves a choice only between CFCs, which will no longer be found on the market, and less efficient products such as F124 or F123.

Other purification processes making use of the same technique have been described in patent applications EP 626 362, WO 9521147, WO 9521148, FR 2 716 449, WO 9606063 and WO 9607627; the extractants employed are hydrocarbons or polar solvents (alcohols, ethers, ketones or esters). In the case where polar solvents are used the selectivity is reversed, that is to say that the compound entrained by the solvent is no longer the impurity (F115) but the product to be purified (F125); this procedure is obviously more clumsy from an industrial viewpoint. Furthermore, all these extractants have the disadvantage of being highly flammable and therefore require industrial plants that are much more costly from the viewpoint of safety.

DESCRIPTION OF THE INVENTION

It has now been found that $C_5$–$C_8$ perfluoroalkyl halides of the RfX type have selectivities for F115 which are higher than those of the chlorofluoroethanes or hydrochlorofluoroethanes, while exhibiting volatilities that are markedly lower than those of these products.

The subject-matter of the present invention is therefore a process for the purification of a pentafluoroethane containing chloropentafluoroethane by extractive distillation, characterized in that the extractant employed is a perfluoroalkyl halide RfX where Rf denotes a linear or branched perfluoroalkyl radical $C_nF_{2n+1}$ containing 5 to 8 carbon atoms and X denotes a chlorine, bromine or iodine atom.

Among these compounds it is preferred to employ the compounds containing six carbon atoms, in which X is a chlorine or bromine atom.

The compounds RfX can be obtained by various methods described in the literature. For the preparation of perfluoroalkyl iodides the most common method is the telomerization of tetrafluoroethylene with pentafluoroethyl iodide. The other halides (X=Cl or Br) are generally prepared by thermal chlorination or bromination of the iodides.

The process according to the invention can be used according to the well known principles of extractive distillation. The operation is performed in an extractive distillation column into which the F125–F115 mixture to be separated is injected at a point situated at the top of the exhaustion section. The extractant, namely the perfluoroalkyl halide, is introduced into the column at a point situated at the top of the absorption section; it travels in the liquid state from its point of introduction to the boiler.

The diameter and the number of stages of the extractive distillation column, the reflux ratio and the optimum temperatures and pressures can be easily calculated by a person skilled in the art from the characteristic data for the individual constituents and for their mixtures (relative volatilities, vapour pressures and physical constants).

EXAMPLES

The following examples, in which the pressures indicated are in bars absolute, illustrate the invention without limiting it.

The suitability of a solvent for being employed in the separation using extractive distillation of a F115–F125 mixture is assessed through its selectivity (S), defined as the ratio of the solubilities of F115 ($S_{115}$) and of F125 ($S_{125}$) in the solvent at a partial pressure of 1.4 bars absolute and at a temperature of 25° C.:

$$S = S_{115}/S_{125}$$

To determine these solubilities a stainless steel autoclave with a capacity of 471 ml is employed, into which a known quantity of solvent is introduced by trapping or direct pouring. After air has been removed, the whole is heated from the temperature of liquid nitrogen to the ambient temperature and then placed in a vessel thermostated at 25° C. The quantities of F115 or of F125 which are needed to obtain a pressure change close to 1.4 bar are then introduced by means of a valve. After equilibration, the total pressure is noted and a sample of the liquid phase and a sample of the gaseous phase are taken using appropriate devices, and are then analysed by gas phase chromatography.

The molar composition of the gaseous phase makes it possible to calculate the partial pressure of F115 or of F125. The solubility of F115 or of F125 in the solvent, expressed in g of F115 or of F125 per liter of solvent in liquid phase, is calculated from the molar composition of the liquid phase using the relationship:

$$S = 1000 \times x \times M \times d'/(x' \times M')$$

in which x and x' denote, respectively, the molar fractions of F115 (or of F125) and of solvent present in the liquid phase (x+x'=1), M and M' denote, respectively, the molecular mass of F115 (or of F125) and that of the solvent, and d' is the density of the solvent in liquid phase at 25° C.

Example 1 (Comparative)

80.2 g of F114 were placed in the measurement cell and 17.2 g of F115 were introduced. After equilibration of the system the total pressure settled out at 3.25 bars and analysis of the liquid and gaseous phases gave the following results:

|  | MOLAR % | |
|---|---|---|
|  | Gas phase | Liquid phase |
| F115 | 43.1 | 15.9 |
| F114 | 56.9 | 84.1 | that is a solubility ($S_{115}$) of 250.9 g of F115 per liter of liquid F114 at 25° C. and at a partial pressure of 1.4 bar of F115.

The operation was repeated with F125 by introducing 6.7 g of F125 into 82.1 g of F114 in a first test and then 10.5 g of F125 into 80.7 g of F114 in a second test. Since the equilibrium pressures are equal to 3.25 and 3.85 bars respectively, the following compositions were observed for the gas and liquid phases of the two systems.

|  | MOLAR % | | | |
|---|---|---|---|---|
|  | Total pressure 3.25 bars | | Total pressure 3.85 bars | |
|  | gas | liquid | gas | liquid |
| F125 | 36.4 | 6.9 | 47 | 10.7 |
| F114 | 63.6 | 93.1 | 53 | 89.3 | that is respective solubilities of 76.2 g/l and 123.3 g/l at the partial pressures of 1.18 and 1.81 bars and an estimated solubility ($S_{125}$) of 93 g/l at 1.4 bars. The selectivity defined by the ratio of the solubilities of F115 and of F125 at the same pressure is therefore equal to 2.72.

Example 2

126.9 g of n-perfluorohexyl chloride $C_6F_{13}Cl$ (b.: 86° C.) were placed in the apparatus described above and 14.9 g of F115 were introduced. After equilibration the pressure stabilized at 1.45 bar and chromatographic analysis of each of the two phases gave the following results.

|  | MOLAR % | |
|---|---|---|
|  | Gas phase | Liquid phase |
| F115 | 93.25 | 15.7 |
| $C_6F_{13}Cl$ | 6.75 | 84.3 |

These results gave a solubility ($S_{115}$) of 142.9 g/l at a partial pressure of 1.4 bars absolute.

The operation was repeated, the F115 being replaced with 6.7 g of F125 which was introduced into 129.7 g of $C_6F_{13}Cl$. After stabilization of the pressure at 1.525 bar the composition of the two phases was the following:

|  | MOLAR % | |
|---|---|---|
|  | Gas phase | Liquid phase |
| F125 | 92.6 | 8 |
| $C_6F_{13}Cl$ | 7.4 | 92 | that is a solubility ($S_{125}$) of 49.6 g/l for a partial pressure of 1.4 bar absolute and a selectivity ($S_{115}/S_{125}$) of 2.88.

Example 3

The same apparatus as in the preceding examples was employed and 136.7 g of n-perfluorohexyl bromide $C_6F_{13}Br$ (b.: 100° C.) and 14.5 g of F115 were introduced successively into the measurement cell. After stabilization of the pressure at 1.425 bars absolute a sample of the gas and liquid phases was taken at the equilibrium and these were analysed by gas phase chromatography after complete vaporization of the liquid sample. The following results were obtained.

|  | MOLAR % | |
|---|---|---|
|  | Gas phase | Liquid phase |
| F115 | 96.45 | 16.2 |
| $C_6F_{13}Cl$ | 3.55 | 83.8 | that is a solubility ($S_{115}$) of 141.8 g/l at a partial pressure of 1.4 bar absolute.

The operation was repeated, the F115 being replaced with 6.7 g of F125, introduced in 137.1 g of $C_6F_{13}Br$. After stirring the pressure reached equilibrium at 1.425 bar at the temperature of 25° C. and the composition of the two phases was the following:

|  | MOLAR % | |
|---|---|---|
|  | Gas phase | Liquid phase |
| F125 | 96.1 | 9.9 |
| $C_6F_{13}Br$ | 3.9 | 90.1 | that is a solubility ($S_{125}$) of 62.8 g/l at 25° C. at a partial pressure of 1.4 bars absolute and a selectivity S of 2.25.

Example 4

A laboratory extractive distillation column of 50 theoretical plates was employed for separating with the aid of n-perfluorohexyl chloride a mixture containing, by weight, 97% of F125 and 3% of F115. This column, shown diagrammatically in FIG. 1, is fed with solvent via the conduit (2) at the seventh theoretical plate at a rate of 35 kg/hour, and the crude F125 is ejected at a rate of 5.2 kg/hour via the conduit (1) at the height of the forty-fourth theoretical plate. The purified F125 was taken out at the top of the extractive distillation column via the conduit (3) and the F115-enriched $C_6F_{13}Cl$ at the bottom via the conduit (4).

The results collated in the following table were obtained by operating at a pressure of 8 bars absolute and with a reflux ratio equal to 6.

| COMPOSITION (by weight) | Charge 1 | Solvent 2 | Top 3 | Bottom 4 |
|---|---|---|---|---|
| F125 | 97% | — | 99.99% | 710 ppm |
| F115 | 3% | — | 90 ppm | 0.4% |
| $C_6F_{13}Cl$ | — | 100% | <5 ppm | 99.5% |

Example 5

The same mixture of F125 and F115 as in Example 4 was separated with the aid of n-perfluorohexyl chloride on an extractive distillation column of 40 theoretical plates, shown diagrammatically in FIG. 1.

The $C_6F_{13}Cl$ was introduced at a rate of 700 kg/hour via the conduit (2) at the fifth theoretical plate and the F125–F115 mixture to be separated was fed at a rate of 66 kg/hour via the conduit (1) onto the thirty-fifth theoretical plate.

The column operated at the pressure of 8 bars absolute and with a reflux ratio equal to 7. The results obtained are collated in the following table.

| COMPOSITION (by weight) | Charge 1 | Solvent 2 | Top 3 | Bottom 4 |
|---|---|---|---|---|
| F125 | 97% | — | 99.99% | 460 ppm |
| F115 | 3% | — | 90 ppm | 0.3% |
| $C_6F_{13}Cl$ | — | 100% | <5 ppm | 99.7% |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the purification of a pentafluoroethane (F125) containing chloropentafluoroethane (F115) by extractive distillation, comprising purifying said pentafluoroethane where the extractant employed is a perfluoroalkyl halide RfX in which Rf denotes a linear or branched radical $C_nF_{2n+1}$ containing 5 to 8 carbon atoms and X is chloride, bromide, or iodide.

2. Process according to claim 1, wherein the halide contains 6 carbon atoms and X is a chloride or bromide.

3. Process according to claim 1, wherein the extractant is n-perfluorohexyl chloride.

* * * * *